United States Patent [19]

Morino et al.

[11] Patent Number: 5,505,944
[45] Date of Patent: Apr. 9, 1996

[54] PHYSIOLOGICALLY ACTIVE SUBSTANCE NK175203, PROCESS FOR PRODUCTION THEREOF AND PHARMACEUTICAL USE THEREOF

[75] Inventors: Tomio Morino, Omiya; Ayako Nakatani, Tokyo; Masayuki Kitagawa, Tokyo; Masaya Sato, Tokyo; Takashi Harada, Tokyo; Seiichi Saito, Kashiwa, all of Japan

[73] Assignee: Nippon Kayaku Kabushiki Kaisha, Tokyo, Japan

[21] Appl. No.: 392,841

[22] PCT Filed: Sep. 8, 1993

[86] PCT No.: JP93/01276

§ 371 Date: Feb. 28, 1995

§ 102(e) Date: Feb. 28, 1995

[87] PCT Pub. No.: WO94/05679

PCT Pub. Date: Mar. 17, 1994

[30] Foreign Application Priority Data

Sep. 9, 1992 [JP] Japan .................................. 4-265646

[51] Int. Cl.$^6$ .............................. C07G 17/00; C12P 1/04; A61K 35/74; C12N 1/20
[52] U.S. Cl. ..................... 424/117; 435/70.2; 435/70.4; 435/170; 435/253.5; 435/886
[58] Field of Search ..................... 424/117; 435/253.5, 435/886, 170, 70.2, 70.4

[56] References Cited

U.S. PATENT DOCUMENTS

| | | | |
|---|---|---|---|
| 4,530,835 | 7/1985 | Bunge et al. | 424/117 |
| 4,623,622 | 11/1986 | Anderson | 435/241 |
| 4,703,008 | 10/1987 | Lin | 435/240.2 |
| 4,822,735 | 4/1989 | Anderson | 435/68 |
| 4,840,934 | 6/1989 | Anderson | 514/2 |
| 5,162,317 | 11/1992 | Hultner et al. | 435/70.3 |
| 5,169,765 | 12/1992 | Borch et al. | 435/70.4 |
| 5,223,605 | 6/1993 | Fanslow et al. | 530/350 |

FOREIGN PATENT DOCUMENTS

| | | |
|---|---|---|
| 0215126 | 3/1987 | European Pat. Off. . |
| 61-501627 | 8/1986 | Japan . |
| 62-236497 | 10/1987 | Japan . |
| 2227089 | 9/1990 | Japan . |
| 85/02610 | 11/1985 | WIPO . |

*Primary Examiner*—Herbert J. Lilling
*Attorney, Agent, or Firm*—Nields & Lemack

[57] ABSTRACT

Physiologically active substance NK175203 is produced by culturing bacteria belonging to the genus Streptomyces and capable of producing the physiologically active substance NK175203, and collecting the produced and accumulated substance. The physiologically active substance NK175203 is useful as an effective ingredient of a pharmaceutical composition for promoting proliferation of bone marrow cells.

5 Claims, 4 Drawing Sheets

PHYSIOLOGICALLY ACTIVE SUBSTANCE NK175203, PROCESS FOR PRODUCTION THEREOF AND PHARMACEUTICAL USE THEREOF

TECHNICAL FIELD

The present invention relates to a novel physiologically active substance, NK175203, or a pharmaceutically acceptable salt thereof. More particularly, the present invention relates to a novel physiologically active substance NK175203 having an activity for promoting proliferation of bone marrow cells, or a salt thereof; a process for production thereof and pharmaceutical use thereof.

BACKGROUND ART

As bone marrow cell growth enhancers, there are known erythropoietin (Miyake, T. et al., J.B.C., 252, 5558, 1977) and G-CSF (Nicola, N. A., *Annu. Rev. Biochem.*, 339, 27–30, 1989). However, these enhancers are protein preparations and thus unsuitable for frequent administrations. Therefore, it has been desired to find a low molecular weight compound having an activity comparable to these substances.

Disclosure of Invention

The present inventors have made various investigations on metabolites of microorganisms. As a result, it has been discovered that one strain belonging to the genus Streptomyces produces a physiologically active substance NK175203 having an activity of promoting proliferation of bone marrow cells.

That is, an object of the present invention is to provide a novel physiologically active substance, NK175203, having physico-chemical properties 1) through 10) described below, or a pharmaceutically acceptable salt thereof.

1) Appearance: colorless powder
2) Molecular weight: FAB-MS(M)+m/z 303
3) Elemental analysis: $C_{12}H_{17}NO_6S \cdot H_2O$

| Calcd. (%) | | Found | |
|---|---|---|---|
| C: | 44.85 | C: | 44.82 |
| H: | 5.96 | H: | 5.87 |
| N: | 4.36 | N: | 4.34 |

4) Soluble in water, sparingly soluble in hexane or chloroform
5) Rf value by silica gel thin layer chromatography: 0.50 in a developing solvent, butanol: acetic acid: water (4: 1: 2)
6) UV absorption spectrum ($H_2O$)

$\lambda_{max}$nm:200

7) IR absorption spectrum (KBr) $cm^{-1}$: 3400, 2950, 1735, 1600, 1400, 1300, 1145, 1040
8) $^1$H-NMR (200 MHz, $D_2O$) δ ppm: 4.30 (1H, dd, J=4.5, 7.8 Hz), 2.97 (1H, dd, J=4.4, 13.6 Hz), 2.92–2.62 (5H, m), 2.50–2.10 (3H, m), 2.00 (3H, s), 1.81 (1H, m)
9) $^{13}$C-NMR (200 MHz, $D_2O$) δ ppm: 226.9 (s), 185.2 (s), 179.9 (s), 176.6 (s), 57.5 (d), 56.0 (d), 52.6 (d), 40.8 (t), 37.9 (t), 33.6 (t), 28.0 (t), 24.8 (q)
10) Color-forming reaction:
    positive for phosphorus molybdate-sulfuric acid and for tolidine-chlorine Another object of the present invention is to provide a process for producing the physiologically active substance NK175203 which comprises culturing a bacterium belonging to the genus Streptomyces and capable of producing the physiologically active substance NK175203 in a medium to produce and accumulate the physiologically active substance NK175203 in the culture broth, and collecting NK175203.

A further object of the present invention is to provide a pharmaceutical composition for promoting proliferation of bone marrow cells, comprising as an effective ingredient the physiologically active substance NK175203 or a pharmaceutically acceptable salt thereof.

A still further object of the present invention is to provide use of the physiologically active substance NK175203 or a pharmaceutically acceptable salt thereof as the effective ingredient of the pharmaceutical composition.

A still further object of the present invention is to provide bacteria belonging to the genus Streptomyces and capable of producing the physiologically active substance NK175203.

BEST MODE FOR CARRYING OUT THE INVENTION

Figure 1:
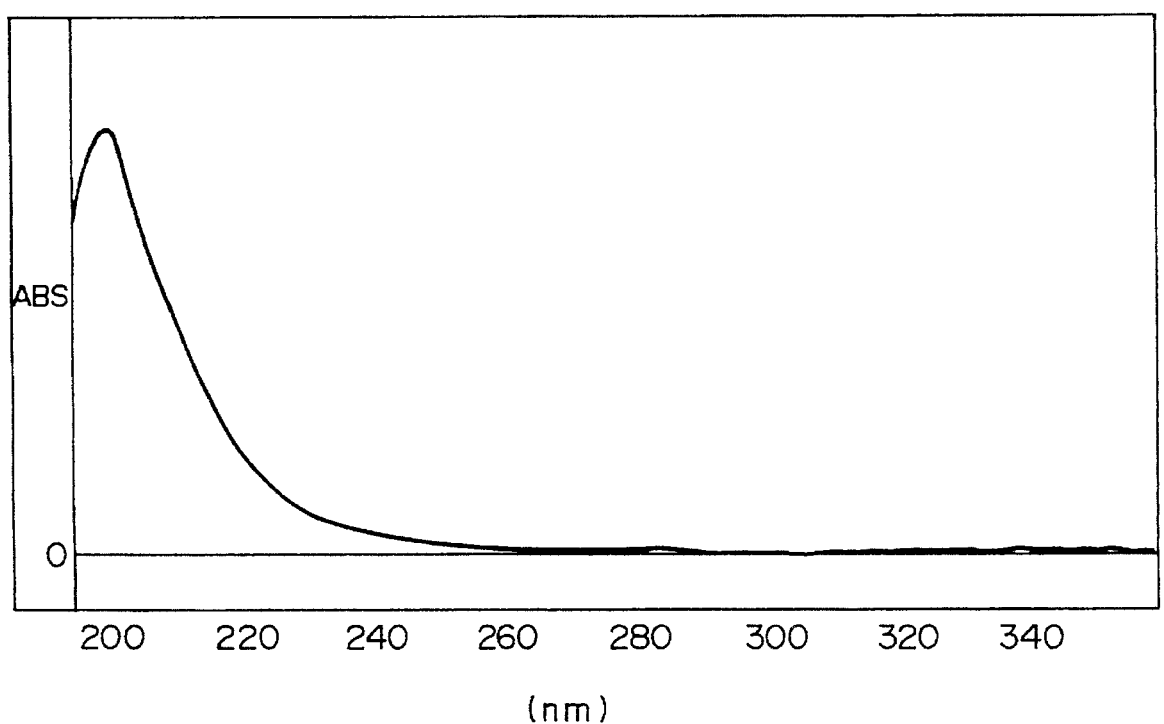
FIG. 1 shows UV spectrum ($H_2O$) of physiologically active substance NK175203.

The physiologically active substance NK175203 which is the compound of the present invention may be a pharmaceutically acceptable salt thereof. Examples of such a salt include salts with alkali metals such as sodium, potassium, etc. and salts with alkaline earth metals such as calcium, and the like.

This novel physiologically active substance NK175203 is obtained by culturing a bacterium belonging to the genus Streptomyces and capable of producing the physiologically active substance NK175203 in a medium to produce and accumulate the physiologically active substance NK175203 in the culture broth, and collecting NK175203. A typical example of the bacteria producing the physiologically active substance NK175203 has the following bacteriological and physiological properties.

1. Morphological properties

Observation after incubation at 27° C. for 2 weeks indicates that aerial mycelia are simply branched and spiral or hook-like at the top. Neither sporangia nor verticillate branch are noted. No zoospore is noted, either. The surface of spores is flat or rough. The spores are cylindrical and have a size of 0.7 to 0.9 ×1.3 μm. The spores are formed in more than 20 chains.

2. Growth in various media

Growth conditions at 27° C. for 2 weeks in various media are shown in Table 1 below.

TABLE 1

| Medium | Growth | Aerial Mycelium |
| --- | --- | --- |
| Sucrose-nitrate agar medium | moderate | moderate, brownish white - light brownish grey - black (hygroscopic) |
| Glucose-asparagine-agar medium | moderate | abundant, brownish white - light brownish grey - black (hygroscopic) |
| Glycerine-asparagine-agar medium | moderate | abundant, brownish white - light brownish grey - black (hygroscopic) |
| Starch-inorganic salt-agar medium | good | moderate, brownish white - light brownish grey - black (hygroscopic) |
| Tyrosine-agar medium | good | moderate, brownish white - light brownish grey - black (hygroscopic) |
| Nutrient-agar medium | moderate | moderate, white |
| Yeast-maltose-agar medium | good | abundant, brownish white - light brownish grey - black (hygroscopic) |
| Oatmeal-agar medium | moderate | moderate, brownish white - light brownish grey - black (hygroscopic) |
| Peptone-yeast-iron-agar medium | moderate | moderate, white |
| Sucrose-nitrate-agar medium | colorless - pale yellow | none |
| Glucose-asparagine-agar medium | pale yellow - brown | slightly brownish |
| Glycerine-asparagine-agar medium | colorless - pale yellow | brownish |
| Starch-inorganic salt-agar medium | pale yellow | slightly brownish |
| Tyrosine-agar medium | pale yellow - pale brown | brownish |
| Nutrient-agar medium | pale yellow | slightly brownish |
| Yeast-maltose-agar medium | colorless | slightly brownish |
| Oatmeal-agar medium | colorless | none |
| Peptone-yeast-iron-agar medium | pale yellow | none |

3. Physiological properties

1) Optimum growth temperature range: 24°–37° C.

2) Reduction of nitrate: negative

3) Liquefaction of gelatin (glucose-peptone-gelatin medium, 20° C.): pseudo-positive 4) Hydrolysis of starch (starch-inorganic salt-agar medium): positive 5) Solidification of skimmed milk: negative 6) Peptonization of skimmed milk: positive 7) Formation of melanoid pigment: negative 4. Assimilation of carbon sources (Pridham-Gottlieb agar medium)

| | |
| --- | --- |
| L-Arabinose | + |
| D-Xylose | + |
| D-Glucose | + |
| D-Fructose | + |
| Sucrose | + |
| Inositol | − |
| L-Rhamnose | − |
| Raffinol | + |
| D-Mannitol | + |

5. Diaminopimelic acid in cell wall LL-diaminopimelic acid

From the foregoing results, the cell wall of this strain is composed of LL-diaminopimelic acid; according to International Streptomyces Project (abbreviated as ISP), the morphology of spore-forming mycelium belongs to section spirales. The surface of spores is flat or rough; the mycelia are of gray color-series and hygroscopic. Melanin-like pigment is not produced. The substrate mycelium shows pale yellow or pale brown. The strain assimilates as carbon sources L-arabinose, D-glucose, D-fructose, sucrose, raffinose, D-mannitol and D-xylose.

Based on the foregoing properties, survey was made according to R. E. Buchanan & N. E. Gibbons, Bergy's Manual of *Determinative Bacteriology*, 8th edition, 1974; the strain NK175203 was found to belong to the genus Streptomyces. Therefore, the strain was named Streptomyces sp. NK175203.

The strain was deposited in National Institute Bioscience and Human-Technology Agency of Industrial Science and Technology (Ibaraki, Japan) on Jul. 10, 1992 and received FERM P-13058 as an accession number. Then the deposition was transferred into an international deposition under the Budapest Treaty on Jul. 28, 1993 and received FERM BP-4372 as an accession number.

In the strain belonging to the genus Streptomyces which is employed in the present invention, its properties are susceptible to change, like other strains belonging to the genus Streptomyces, and thus readily mutated by artificial mutation using, e.g., UV rays, X rays or chemicals. Any mutant can be used for the present invention so long as it is capable of producing the physiologically active substance NK175203 of the present invention.

For producing the physiologically active substance NK175203 according to the present invention, the strain described above is aerobically incubated in a medium containing nutrients Streptomyces can assimilate. As nutrient sources, known nutrients heretofore used for incubation of Streptomyces can be employed. As carbon sources, there may be used, alone or in combination, glucose, fructose, glycerine, sucrose, dextrin, galactose, organic acids, etc.

As inorganic and organic nitrogen sources, there may be employed, alone or in combination, ammonium chloride, ammonium sulfate, urea, ammonium nitrate, sodium nitrate, peptone, meat extract, yeast extract, dry yeast, corn steep liquor, soybean powder, cotton seed lees, Casamino acid, bacto-soyton, soluble vegetable protein, oatmeal, etc.

In addition, inorganic salts such as sodium chloride, calcium carbonate, magnesium sulfate, copper sulfate, iron sulfate, zinc sulfate, manganese chloride, phosphoric acid salts, etc. may also be supplemented, if necessary. Furthermore, organic materials such as amino acids, vitamins, nucleic acids and inorganics may also be supplemented appropriately.

For incubation, liquid culture, especially deep spinner culture is most suited. It is desired to perform incubation at a temperature of 15° C. to 35° C. at a pH of neutral to slightly acidic range.

In liquid culture, incubation generally for 3 to 5 days results in production and accumulation of the substance NK175203 in the culture broth. Incubation is discontinued at the time when the amount of the substance produced reached the maximum. The cells are then separated from the medium by filtration and the product is purified and isolated.

For purification and isolation of the product from the filtrate, a conventional method for separation and purification of a metabolite from a microorganism from the cultured cells is utilized.

That is, the culture broth is separated into the filtrate and the cells by conventional filtration.

NaCl is added to the resulting filtrate in a final concentration of 3% and adsorbed onto a carbon-adsorbed column. After washing with 3% NaCl solution, elution is performed with distilled water. The thus obtained active fraction is concentrated to dryness in vacuum. Then, the residue is subjected to silica gel column chromatography developed with butanol: acetic acid: water, LH-20 column chromatography and preparative high performance liquid chromatography, in this order, to collect the active fraction. Finally, the active fraction is desalted by applying on a carbon-adsorbed column to obtain NK175203 as a colorless substance.

The physiologically active substance NK175203 or its pharmaceutically acceptable salts of the present invention are expected to be pharmaceuticals having an activity of promoting proliferation of bone marrow cells, as will be later described.

Where the substance of the present invention is used as a pharmaceutical, various known methods are applied to preparing its pharmaceutical composition and its administration. The substance may be given by injection, orally, rectally, etc. The pharmaceutical preparations may be in the form of injection, powders, granules, capsules, tablets, suppository, etc.

A variety of auxiliary agents acceptable for pharmaceuticals, i.e., carriers and other aids, e.g., stabilizers, preservatives, pain killers, emulsifiers, etc. may be used, if necessary, so long as they do not adversely affect the physiologically active substance NK175203 or pharmaceutically acceptable salts thereof in making pharmaceutical preparations.

In the pharmaceutical preparation, the content of the physiologically active substance NK175203 or pharmaceutically acceptable salts thereof may be varied in a wide range, depending upon the form of pharmaceutical preparation. The pharmaceutical composition contains the physiologically active substance NK175203 or pharmaceutically acceptable salts thereof generally in the range of 0.01 to 100% (by weight), preferably 0.1 to 70% (by weight); the balance being a carrier and other auxiliary agents conventionally used for pharmaceuticals.

A dose of the physiologically active substance NK175203 or pharmaceutically acceptable salts may be varied depending upon conditions, etc. but is in the range of approximately 0.01 to 800 mg a day per adult. Where consecutive administration is required, it is preferred to reduce a daily dose.

Next, the present invention is described in more detail, by referring to Test Examples, Examples and Preparation Examples.

Test Example 1

Activity On Bone Marrow Cells

The femur was withdrawn from C57BL/6 mouse (10 weeks old) and the bone marrow cells were washed out in Eagle's MEM medium. After allowing to stand at 37° C. for 2 hours in 5% $CO_2$, the supernatant was gently taken to recover the suspended cells alone. The cells were centrifuged at 1200 rpm for 5 minutes to collect the cells. After rinsing with α-MEM medium, the cells were suspended in 20% FBS-containing α-MEM medium. The thus obtained bone marrow cells were inoculated on a 96-well plate in a concentration of $7.5 \times 10^5$ cells/200 μl/well, together with the physiologically active substance NK175203 of the present invention or GM-CSF (Lantrell, M. A. et al., *Proc. Natl. Acad. Sci.*, 8.2, 6250–6254, 1985). Incubation was then performed at 37° C. for 112 hours in 5% $CO_2$. Finally $^3$H-thymidine of 37 KBq was added to the system. After culturing for 8 hours, uptake of $^3$H-thymidine into the cells was determined by a liquid scintillation counter.

The results are shown in Table 2.

TABLE 2

| | Bone marrow cell proliferation activity of physiologically active substance NK175203 | | |
|---|---|---|---|
| GM-CSF | NK175203 | Uptake of [$^3$H]-Thymidine | |
| U/ml | (μg/ml) | mean ± standard error | % |
| 0 | 0 | 860.2 ± 416.4 | 100 |
| | 0.01 | 1106.7 ± 84.5 | 128.7 |
| | 0.1 | 892.2 ± 248.1 | 103.7 |
| | 1 | 881.2 ± 506.2 | 102.4 |
| | 10 | 600.6 ± 21.2 | 69.8 |
| | 100 | 397.3 ± 84.9 | 46.2 |
| 100 | 0 | 33484.4 ± 2136.1 | 100 |
| | 0.01 | 4339687 ± 11996.2 | 129.4 |
| | 0.1 | 63397.1 ± 1185.5 | 189.3 |
| | 1 | 43470.0 ± 1065.3 | 129.8 |
| | 10 | 74630.0 ± 10118.7 | 222.9 |
| | 100 | 531.1 ± 18.5 | 1.6 |

The results reveal that the physiologically active substance NK175203 of the present invention exhibits the activity of promoting proliferation of bone marrow cells at a low concentration and that in the presence of 100 U/ml of GM-CSF, the substance synergetically promotes the proliferation.

Test Example 2

Activity On Cytokine Production Induction

Human leukemia cell line TF-1 (Mckenzie, A. N. J., *Proc. Natl. Acad. Sci.*, 90, 3735–3739, 1993) was inoculated on 10% FCS-RPMI 1640 medium containing 20 μg/ml of the physiologically active substance NK175203 of the present invention, followed by incubation at 37° C. in 5% $CO_2$. The culture supernatant was collected with passage of time, i.e., 1, 2 and 3 days. The amount of cytokine (pg/ml) contained was determined by ELISA (manufactured by Amersham) (Amersham Biotrackprotocol, RPN2143, 2145 and 2151). The results are shown in Table 3.

For control, a case using phosphate buffer alone was determined as a comparison.

TABLE 3

| | Amount of cytokine produced by the addition of NK175203 (unit: pg/ml) | | | | | |
|---|---|---|---|---|---|---|
| | GM-CSF | | IL-6 | | IL-3 | |
| Day | Control | NK175203 | Control | NK175203 | Control | NK175203 |
| 1 | 6.8 | 10.5 | 0.4 | 4.2 | 0 | 13.2 |
| 2 | 7.5 | 20.3 | — | — | — | — |
| 3 | 7.1 | 19.7 | — | — | — | — |

These results reveal that the physiologically active substance NK175203 of the present invention induces the production of cytokines such as GM-CSF, IL-6 (Kishimoto, T., *Blood*, 74, 1–10, 1989), IL-3 [Ihle, J. N., *The Year in Immunology*, 1988 (Crume, J. M. et al., Eds), New York, Karger, 59–102, 1989], etc.

EXAMPLE 1

Preparation of physiologically active substance NK175203

(1) Fermentation

A 100 ml aliquot of seed culture medium having the formulation below was charged in an Erlenmeyer flask of 500 ml volume and sterilized at 120° C. for 20 minutes in an autoclave. One platinum loop of strain NK175203 (FERM P-13058) was inoculated on the medium and cultured at 27° C. for 2 days at 200 rpm, which was made yeast culture.

| Composition of seed culture medium: | |
|---|---|
| Glycerine | 2% |
| Glucose | 0.5% |
| Soybean meal (Sanritti Showa ®) | 1.5% |
| Peptone | 0.5% |
| Yeast extract | 0.05% |
| $MgSO_4$ | 0.005% |
| $K_2HPO_4$ | 0.05% |
| $CaCO_3$ | 0.2% |
| pH = 7.0, adjusted with NaOH | |

In main culture, a 100 ml aliquot of medium having the following composition was charged in an Erlenmeyer flask of 500 ml volume and sterilized at 120° C. for 20 minutes in an autoclave. After 2 ml each of the yeast culture broth previously prepared was inoculated on 100 flasks with the medium, incubation was carried out at 27° C. for 4 days at 200 rpm. The cultured broth of 10 liters thus obtained was filtered through a filter press to obtain the filtrate.

| Main culture medium: | |
|---|---|
| Glucose | 2% |
| Soluble starch | 1% |
| Yeast extract | 1% |
| NZ amine | 0.7% |
| $CaCO_3$ | 0.5% |
| pH = 7.0, adjusted with NaOH | |

(2) Purification

NaCl was added to 9 liters of the thus obtained filtrate in a final concentration of 9%. The mixture was adsorbed at 4° C. onto a column adsorbed with 2 liters of carbon. After washing with 4 liters of 3% NaCl solution, the temperature was reverted to room temperature and the active component was eluted with distilled water. The active component was concentrated to dryness in vacuum. The residue was subjected to column chromatography packed with 500 ml of silica gel, which was developed with butanol: acetic acid: water = 10 : 1 : 2. The active fraction thus obtained was concentrated and 0.75 g of the concentrate was subjected to 800 ml LH-20 gel filtration column chromatography developed with 20% MeOH aqueous solution to obtain 103 mg of the active fraction.

Figure 2:
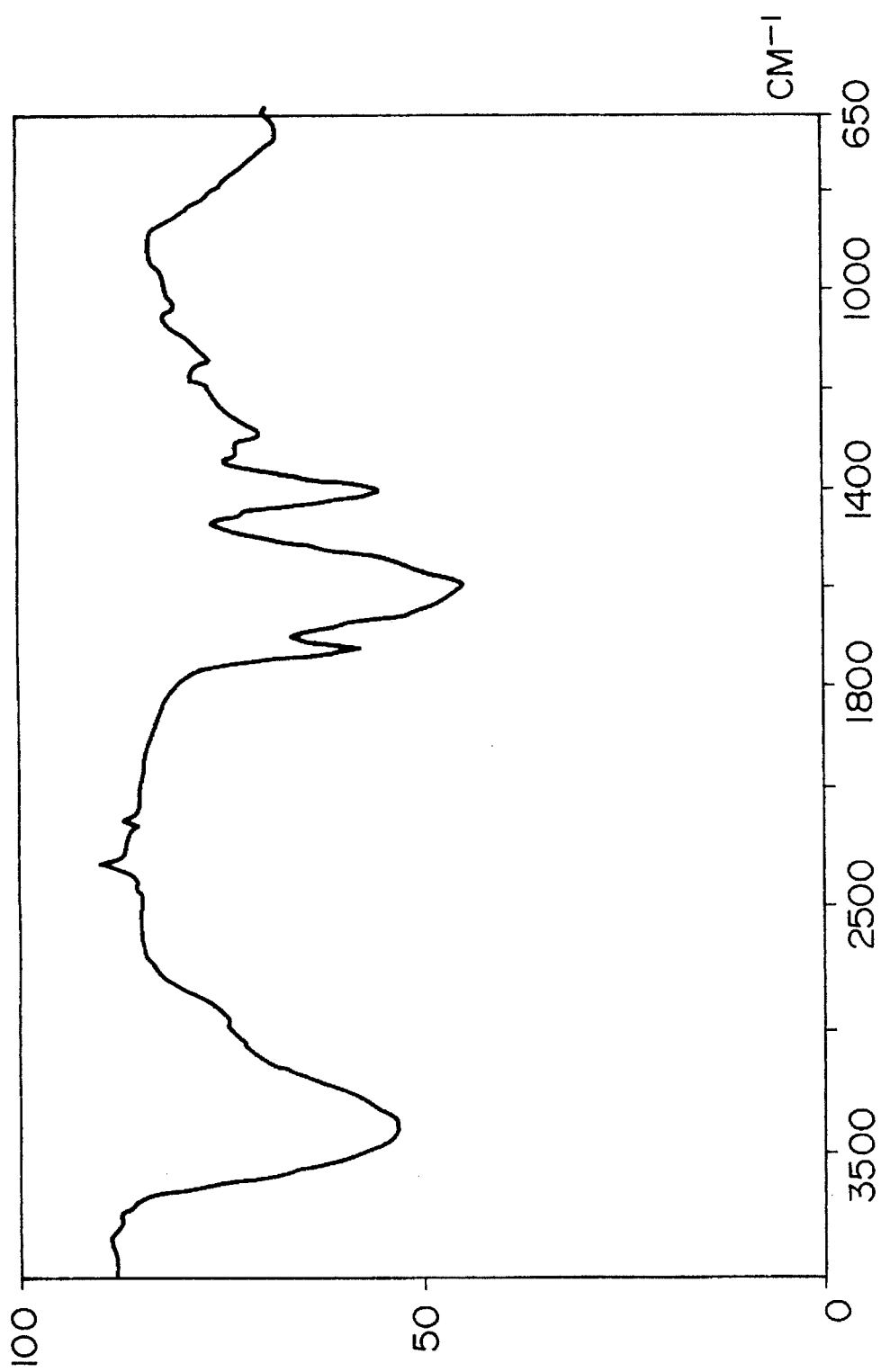
FIG. 2 shows IR spectrum (KBr) of physiologically active substance NK175203.
Figure 3:
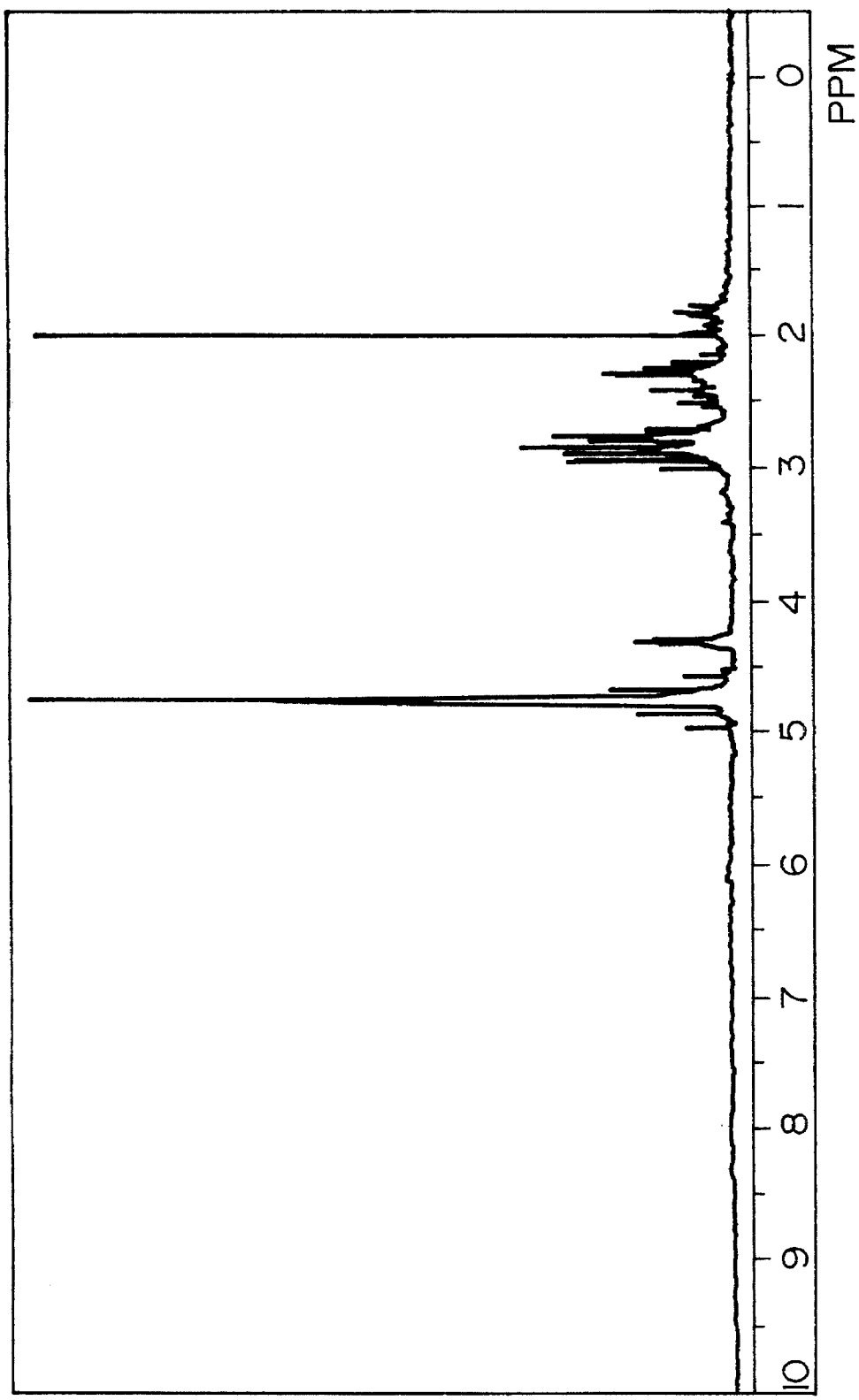
FIG. 3 shows $^1$H-NMR (200 MHz, $D_2O$) of physiologically active substance NK175203.
Figure 4:
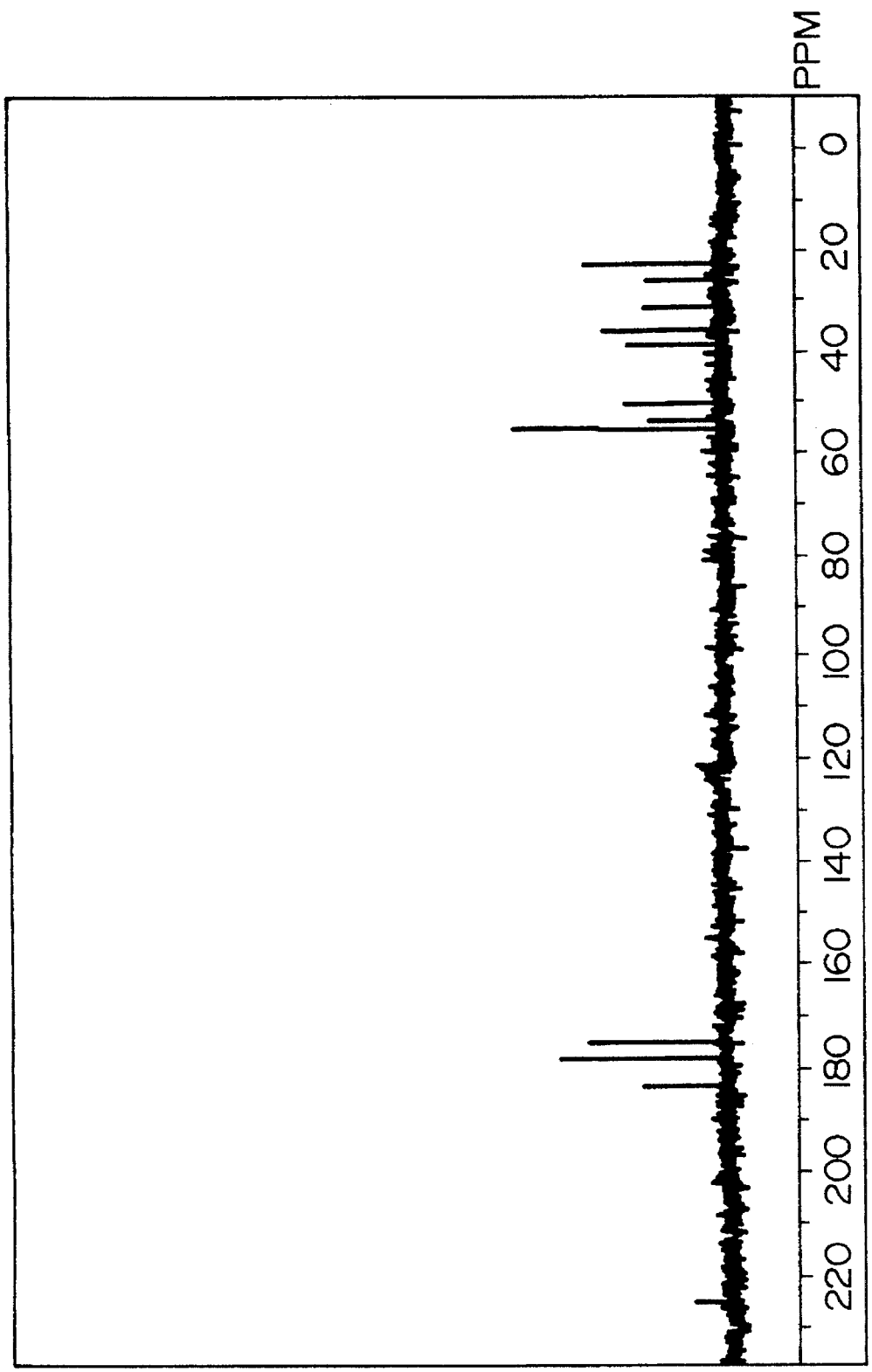
FIG. 4 shows $^{13}$C-NMR (200 MHz, $D_2O$) of physiologically active substance NK175203.

The active fraction was then subjected to preparative high performance liquid chromatography. The active component appearing at retention time of 22.7 minutes was fractionated. The conditions were: moving phase, 2% acetonitrile-1% phosphoric acid, flow rate: 3 ml/min, temperature: 40° C., wavelength for detection: 220 nm, column: Wakosil 115C28AR, column size: 10.0×250 mm. The thus obtained fraction was subjected to a column adsorbed with 20 cc of carbon in the method described above for desalting. The eluate was solidified to dryness to give 70 mg of the physiologically active substance NK175203. UV spectrum ($H_2O$), IR spectrum (KBr), $^1$H-NMR (200 MHz, $D_{20}O$) and $^{13}$C-NMR (200 MHz, $D_2O$) of the physiologically active substance NK175203 are shown in FIGS. 1, 2, 3 and 4, respectively.

The thus obtained physiologically active substance NK175203 showed the following physicochemical properties 1) through 10).

1) Appearance: colorless powder
2) Molecular weight: FAB-MS(M)+m/z 303
3) Elemental analysis: $C_{12}H_{17}NO_6S \cdot H_2O$

| Calcd. (%) | | Found | |
|---|---|---|---|
| C: | 44.85 | C: | 44.82 |
| H: | 5.96 | H: | 5.87 |
| N: | 4.36 | N: | 4.34 |

4) Soluble in water, sparingly soluble in hexane or chloroform
5) Rf value by silica gel thin layer chromatography: 0.50 in a developing solvent, butanol: acetic acid: water (4: 1: 2)
6) UV absorption spectrum ($H_2O$)

$\lambda_{max}$nm:200

7) IR absorption spectrum (KBr) $cm^{-1}$: 3400, 2950, 1735, 1600, 1400, 1300, 1145, 1040
8) $^1$H-NMR (200 MHz, $D_2O$) δ ppm: 4.30 ($^1$H, dd, J=4.5, 7.8 Hz), 2.97 (1H, dd, J=4.4, 13.6 Hz), 2.92–2.62 (5H, m), 2.50–2.10 (3H, m), 2.00 (3H, s), 1.81 (1H, m)
9) $^{13}$C-NMR (200 MHz, $D_2O$) δ ppm: 226.9 (s), 185.2 (s), 179.9 (s), 176.6 (s), 57.5 (d), 56.0 (d), 52.6 (d), 40.8 (t), 37.9 (t), 33.6 (t), 28.0 (t), 24.8 (q)
10) Color-forming reaction: positive for phosphorus molybdate-sulfuric acid and for tolidine-chlorine Preparation Example 1

Preparation of granules

After 50 parts by weight of the physiologically active substance NK175203 sodium salt, 600 parts by weight of lactose, 330 parts by weight of crystalline cellulose and 20 parts by weight of hydroxypropyl cellulose were thoroughly kneaded, the mixture was compressed with a roller compactor TM, ground and sieved through a sieve between 19 mesh and 16 mesh to obtain granules.

Preparation Example 2

Preparation of tablets

After 100 parts by weight of the physiologically active substance NK175203 sodium salt, 90 parts by weight of crystalline lactose, 107 parts by weight of crystalline cellulose and 3 parts by weight of magnesium stearate were kneaded with a V-mixer, the mixture was tableted to give tablets, one being 300 mg.

Preparation Example 3

Preparation of injection

Distilled water was added to 50 parts by weight of the physiologically active substance NK175203 sodium salt and 120 parts by weight of mannitol to make the whole volume 2000 parts. The mixture was dissolved in distilled water. The solution was aseptically filtered through a millipore filter Type GS. Two grams of the filtrate was taken in a vial of 10 ml and freeze-dried to give a freeze-dried injection containing 50 mg of sodium salt of the compound per vial.

Industrial Applicability

The novel physiologically active substance NK175203 or salts thereof provided by the present invention possess an activity of promoting proliferation of bone marrow cells. Therefore, the substance is useful as an effective component for, e.g., a bone marrow cell enhancer.

We claim:

1. Physiologically active substance NK175203 having the following physicochemical properties, or a pharmaceutically acceptable salt thereof 1) Appearance: colorless powder
   2) Molecular weight: FAB-MS(M)+m/z 303
   3) Elemental analysis: $C_{12}H_{17}NO_6S \cdot H_2O$

| Calcd. (%) | | Found | |
   |---|---|---|---|
   | C: | 44.85 | C: | 44.82 |
   | H: | 5.96 | H: | 5.87 |
   | N: | 4.36 | N: | 4.34 |

4) Soluble in water, sparingly soluble in hexane or chloroform
   5) Rf value by silica gel thin layer chromatography: 0.50 in a developing solvent, butanol:acetic acid: water (4:1:2)
   6) UV absorption spectrum ($H_2O$)

$\lambda_{max}$nm:200

7) IR absorption spectrum (KBr) $cm^{-1}$: 3400, 2950, 1735, 1600, 1400, 1300, 1145, 1040
   8) $^1$H-NMR (200 MHz, $D_2O$) δ ppm: 4.30 (1H, dd, J=4.5, 7.8 Hz), 2.97 (1H, dd, J=4.4, 13.6 Hz), 2.92–2.62 (5H, m), 2.50–2.10 (3H, m), 2.00 (3H, s), 1.81 (1H, m)
   9) $^{13}$C-NMR (200 MHz, $D_2O$) δ ppm: 226.9 (s), 185.2 (s), 179.9 (s), 176.6 (s), 57.5 (d), 56.0 (d), 52.6 (d), 40.8 (t), 37.9 (t), 33.6 (t), 28.0 (t), 24.8 (q)
   10) Color-forming reaction: positive for phosphorus molybdate-sulfuric acid and for tolidine-chlorine.

2. A process for producing physiologically active substance NK175203 which comprises culturing a bacterium belonging to the genus Streptomyces and capable of producing the physiologically active substance NK175203 of claim 1 in a medium to produce and accumulate the physiologically active substance NK175203 in the culture broth, and collecting NK175203.

3. A pharmaceutical composition for promoting proliferation of bone marrow cells, comprising as an effective ingredient the physiologically active substance NK175203 or a pharmaceutically acceptable salt thereof according to claim 1, and pharmaceutically acceptable carriers.

4. A method for promoting proliferation of bone marrow cells which comprises administering an effective dose of the physiologically active substance NK175203 or a pharmaceutically acceptable salt thereof according to claim 1.

5. A biological pure strain of Streptomyces sp. NK175203 or mutant thereof capable of producing the physiologically active substance NK175203 according to claim 1.

* * * * *